United States Patent [19]

Vandervalk et al.

[11] Patent Number: 5,623,427

[45] Date of Patent: Apr. 22, 1997

[54] NONDESTRUCTIVE ANODIC CAPACITY GAUGE

[75] Inventors: Leon Vandervalk, Prescott, Canada; Frank J. Koch, Ogdensburg, N.Y.

[73] Assignee: DeFelsko Corporation, Ogdensburg, N.Y.

[21] Appl. No.: 300,188

[22] Filed: Sep. 2, 1994

[51] Int. Cl.⁶ .................................................. G01R 27/26
[52] U.S. Cl. .......................... 364/563; 324/229; 324/230; 427/10
[58] Field of Search ............................ 364/563; 324/202, 324/228, 229, 230, 654, 662, 671; 33/834; 205/791; 427/9, 10

[56] References Cited

U.S. PATENT DOCUMENTS

| | | | |
|---|---|---|---|
| 3,801,900 | 4/1974 | Szasz | 324/671 |
| 3,986,105 | 10/1976 | Nix et al. | 324/230 |
| 4,495,558 | 1/1985 | Cath et al. | 364/563 |
| 4,507,609 | 3/1985 | Madewell | 324/230 |
| 4,510,577 | 4/1985 | Tsujii et al. | 364/563 |
| 4,556,846 | 12/1985 | D'Hondt | 324/202 |
| 4,593,244 | 6/1986 | Summers et al. | 324/230 |
| 4,695,797 | 9/1987 | Deutsch et al. | 427/10 |
| 4,715,007 | 12/1987 | Fujita et al. | 364/563 |
| 4,752,739 | 6/1988 | Wang | 324/230 |
| 4,806,849 | 2/1989 | Kihira et al. | 427/10 |
| 4,843,319 | 6/1989 | Lara | 324/240 |
| 4,843,320 | 6/1989 | Spies | 324/229 |
| 4,849,694 | 7/1989 | Coates | 324/230 |
| 4,851,774 | 7/1989 | Törnblom | 324/225 |
| 4,855,677 | 8/1989 | Clark, Jr. et al. | 324/238 |
| 4,893,079 | 1/1990 | Kustra et al. | 324/225 |
| 4,922,201 | 5/1990 | Vernon et al. | 324/236 |
| 5,091,696 | 2/1992 | Koosen | 324/229 |
| 5,124,641 | 6/1992 | Netter et al. | 324/202 |
| 5,142,228 | 8/1992 | Kingsbury | 324/230 |
| 5,191,286 | 3/1993 | Fischer | 324/230 |
| 5,241,280 | 8/1993 | Aidun et al. | 324/671 |
| 5,303,169 | 4/1994 | Baker | 364/563 |
| 5,453,689 | 9/1995 | Goldfine et al. | 324/230 |

FOREIGN PATENT DOCUMENTS

| | | |
|---|---|---|
| 170341 | 2/1986 | European Pat. Off. . |
| 1312710 | 4/1973 | United Kingdom . |
| 2265985 | 10/1993 | United Kingdom . |

OTHER PUBLICATIONS

*Eddy Current Testing Manual on Eddy Current Method*, Atomic Energy of Canada Limited, V.S. Cecco et al., vol. 1, pp. 69–78 (Nov. 1981).
*6000 Series*, Coating Thickness Gage—Instructions (Manual), pp. 1–26, DeFelsko Corporation (1993).
*PosiTector® 6000 Series*, one–page advertisement, DeFelsko Corporation (1992).
*Eddy Current Techniques in Nondestructive Evaluation*, "Fundamental Eddy Current Concepts", Don E. Bray, pp. 525–532.
*Thickness Measurement*, two–page advertisement, FaAA Products Division.
*NORTEC 23ST* Mini Eddyscope, two–page advertisement, Staveley Instruments Inc.
*NORTEC—Eddy Current Probes*, Leadership in Non Destructive Testing, pp. 4–7, Staveley Instruments Inc.
*Eagle Plus*, Uniwest (brochure).

*Primary Examiner*—Emanuel T. Voeltz
*Assistant Examiner*—Eric W. Stamber
*Attorney, Agent, or Firm*—Burns, Doane, Swecker & Mathis, L.L.P.

[57] ABSTRACT

A method and apparatus for measuring an anodic capacity of a thermally sprayed coating are described. Eddy current techniques are used to probe the coating and resulting RMS voltages are translated into anodic capacity indications which can be standardized or absolute. Recalibration can be achieved using single point measurement.

10 Claims, 4 Drawing Sheets

NONDESTRUCTIVE ANODIC CAPACITY GAUGE

BACKGROUND

The present invention relates generally to measurement devices and, more particularly, to devices which measure anodic capacity in metallic layers.

The application of conductive coatings to rebar reinforced concrete is a technique used to arrest the degradation of reinforced concrete structures. By this technique, a conductive coating is applied to a concrete structure to form a galvanic sacrificial coating. The coating serves as an anode in both passive and active impressed (rectified AC) or galvanic (DC) cathodic protection. Typical conductive coatings in use today include zinc and zinc/aluminum alloys. These coatings are especially suited for use in areas where an electrolyte can leach into the concrete, for example in underground and underwater structures. The coatings are typically applied to the structure using a thermal spray system in which the coating is melted under intense heat and propelled onto the target structure to solidify.

The service life or "anodic capacity" of the coating can be roughly approximated by the thickness of the coating. Accordingly, during the coating application, measurements of applied coating thickness can be useful in estimating whether adequate anodic capacity is being applied. Similarly, during the service life of a coated structure, the remaining anodic protection can be estimated by measuring the remaining coating thickness at regular intervals.

Because so many reinforced concrete structures benefit from this form of protection there is an increasing need to accurately measure the remaining anodic protection capacity of such coatings at various points during the life cycle of the anodic layer. Conventionally, however, the measurement of applied anodic capacity and remaining anodic capacity typically involved measuring anode thickness using destructive techniques in which the protective coatings are damaged and subsequently repaired. Several such destructive techniques are described below.

One way in which the initial thickness of an anodic layer has conventionally been measured is to place masking tape over the uncoated concrete, apply zinc to the concrete, and then remove the zinc-covered tape. The thickness of the zinc layer can then be measured by removing the tape from the concrete, using calipers or a micrometer to measure the thickness of the zinc and tape, and subtracting the thickness of the tape. In the same way, a steel coupon can be adhered to the concrete prior to spraying the zinc and subsequently removed. The zinc and steel thickness are then measured using an electronic or magnetic gauge, or using the mechanical gauges described earlier for measuring the zinc on the masking tape.

Another way in which the thickness of a conductive coating can be determined is by measuring electrical resistance. Using a four conductor probe configured to measure surface resistance one can accurately measure the thickness of a conductive coating applied to a nonconductive substrate. The four contact surface probe can be used to apply a known current to the surface of the coating and resistivity can be determined by measuring the voltage drop across a known distance. The thickness of the coating can then be correlated to resistivity. However, this technique requires that electrical contact be made with the surface of the coating, which may prove difficult when measuring, for example, the remaining anodic capacity of partially corroded coatings that are covered with non-conductive corrosion. Thus, to measure the remaining anodic capacity of an anode that has been in service would require that the coating be removed for visual inspection to determine how much of the pure zinc layer remains.

These destructive approaches are of course undesirable since they reduce the effectiveness of the protective zinc layer by creating openings. In order to overcome this problem, non-destructive methods for determining zinc layer characteristics have been proposed. For example, eddy currents have been used to measure conductive material thickness per se in a nondestructive manner.

This method utilizes a first coil to generate a magnetic field which induces an eddy current in the conductive material. The eddy current, in turn, creates a second magnetic field which is sensed by a second coil. The voltage induced in the second coil can then be correlated to the thickness of the conductive material. Simply knowing the thickness of the material, however, is insufficient to accurately determine its remaining anodic capacity since other factors, such as the density of the material, also impact on this determination.

Thus, conventional methods and apparatuses fail to provide a nondestructive way of determining how much longer the protection provided by the zinc layer to the concrete will last. Moreover, known instruments do not measure the anodic capacity of an anode and represent this quantity in standardized units that are meaningful to an operator.

Furthermore, conventional eddy current devices cannot be calibrated to measure the anodic capacity of an anode, for example, using the coating characteristics of the applied conductive material.

SUMMARY

These and other drawbacks and limitations associated with conventional techniques are overcome according to the present invention. Exemplary embodiments thereof apply eddy current techniques to non-destructively measure the anodic capacity of an anode used in cathodic protection. Exemplary embodiments illustrate how the present invention can be applied to instruments which can be specifically designed and calibrated to measure anodic capacity of a material such as thermally sprayed zinc or zinc alloys and to compensate for liftoff due to corrosion, roughness, pitting and various coating characteristics. Exemplary instruments can be calibrated to measure the equivalent pure zinc anodic capacity for an impure coating in standardized units, for example, zinc mils (or zinc μm). Alternative units of measure can be displayed by the instrument as required by the operator. The operator of equipment according to the present invention thus can gauge the anodic capacity of the coating in terms that are easily understood and communicated.

BRIEF DESCRIPTION OF THE DRAWINGS

The foregoing, and other, objects, features and advantages of the present invention will be more readily understood upon reading the following detailed description in conjunction with the drawings in which.

DETAILED DESCRIPTION

Figure 1:
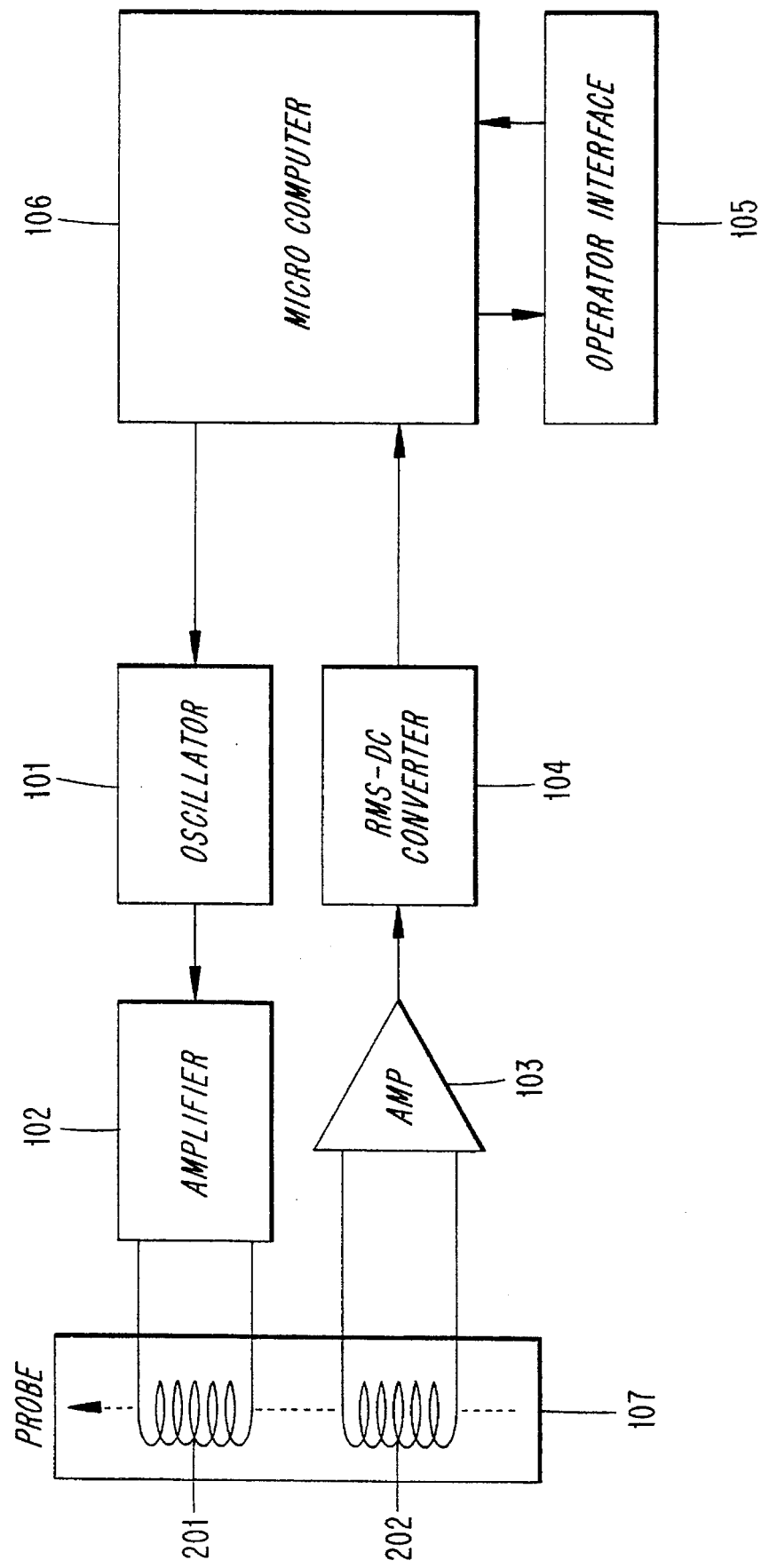
FIG. 1 illustrates an exemplary non-destructive anodic capacity gauge according to an exemplary embodiment of the present invention.

The following exemplary embodiments of the present invention are characterized in terms of zinc coatings and apparatuses and methods for measuring the anodic capacity of such coatings. However, those skilled in the art will readily appreciate that the present invention can also be applied in a similar manner to other types of coatings, such as titanium coatings and zinc/aluminum coatings.

Corrosion of metal reinforcement bars ("rebars") used to reinforce concrete structures occurs when the rebar comes into contact with an electrolyte, for example sodium chloride, dissolved in water. The differences in electrical potential that develop between localized areas of the rebar surface cause currents to flow from the cathodic (less reactive) areas to the anodic (more reactive) areas through the rebar and from the anodic to the cathodic areas through the electrolyte. In the case of dissolved sodium chloride, for example, sodium ions migrate to the negative electrode and the chloride ions migrate to the positive electrode, causing a current of electricity to flow. When the current enters the electrolyte from the rebar, metal ions go into solution. The metal ions form compounds with the surrounding atoms, thus causing anodic corrosion. In the case of steel rebar an exemplary chemical reaction can be described as follows:

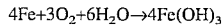

$$4Fe+3O_2+6H_2O \rightarrow 4Fe(OH)_3$$

The iron combines with both water and oxygen to form hydrated iron oxide which is a relatively weak and brittle material. Since some of the reinforcing steel has been transformed into hydrated iron oxide, the overall structure is weakened. However, several techniques can be applied to reduce such corrosion. For example, the iron rebar can be alloyed with chromium or chromium and nickel to form stainless steel rebar. Although this would work well, the expense is commercially prohibitive.

Another possibility is forming the rebar from, for example, galvanized iron, i.e., iron or steel coated with a layer of zinc for protection against corrosion. With this method, in the presence of corrosive solutions, an electric potential is set up between the zinc and iron. The zinc coating forms an anode and will thus corrode before the iron. This technique is generally more attractive than creating stainless steel rebar since zinc can be applied with greater ease and at lower cost than other metallic coatings such as tin, chromium, nickel, or aluminum.

A further possibility is to apply a conductive coating such as zinc to the concrete structure. For example, molten zinc can be applied in the form of a fine spray to concrete rebar in several ways. One such spray system uses an electric arc to melt the materials to be sprayed. In this type of system the zinc or zinc alloy is fed by wire to an arc chamber where a positively charged wire, for example a zinc wire, is brought into close proximity to a negatively charged wire, for example a zinc/aluminum alloy wire. If there is sufficient potential (e.g., 26 volts at 300 amps) between the wires an arc is formed. The intense heat created by the arc will in turn liquefy the wires. A stream of air under high pressure (e.g., 75 PSI) is used to propel the liquid metal onto the target structure. The metal then solidifies thereby forming a conductive coating. To build up a coating the operator of the spray equipment can control arc voltage, spray distance and the distance between overlapping passes. The coating becomes a sacrificial anode for cathodic protection which is electrically connected to the rebar so that the anode corrodes instead of the rebar.

When the structure comes into contact with an electrolyte, the zinc anode releases zinc ions into the solution. If the electrolyte is, for example, dissolved sodium chloride then chloride ions will migrate towards the zinc anode and react with the zinc ions to form byproducts, such as zinc chloride ($ZnCl_2$). $ZnCl_2$ is nonconductive and forms on the surface of the zinc exposed to the electrolyte. The anode thus provides protection to the rebar within the reinforced concrete structure.

However, as the zinc reacts with electrolytes, the coating becomes an impure hybrid of zinc and reaction products. As this occurs, the ability of the zinc layer to provide protection to the rebar diminishes. When all of the pure zinc is gone, the rebar will then begin to react with electrolytes. This ability of the zinc layer to provide protection is termed herein "anodic capacity". The measurement of anodic capacity according to the present invention provides the desirable result of giving inspectors a quantifiable and understandable output which accurately indicates how much more protection the zinc layer can provide.

According to exemplary embodiments of the present invention, an eddy current technique is used to measure the anodic capacity of zinc applied to structurally reinforced concrete structures. The anodic capacity of the coating is determined by measuring the quantity of pure zinc beneath the eddy current sensor and by compensating for any liftoff produced by, for example, reaction byproducts such as $ZnCl_2$. The amount of pure zinc present is then converted into equivalent Zn thickness units given by, for example, Zn mils or Zn μms. Alternatively, units of Zn $g/m^2$ or Zn $oz/ft^2$ can be used to express the anodic capacity. Although no specific standard has yet been promulgated for anodic protection measurement in the industry, it is believed that some density parameter will be implicit in these standardized units. Thus, the Zn mil can be used as a reference to compare zinc coating thickness to known calibration standards and an operator can gauge zinc thickness in units of measure that are easily understood and communicated.

Figure 2:
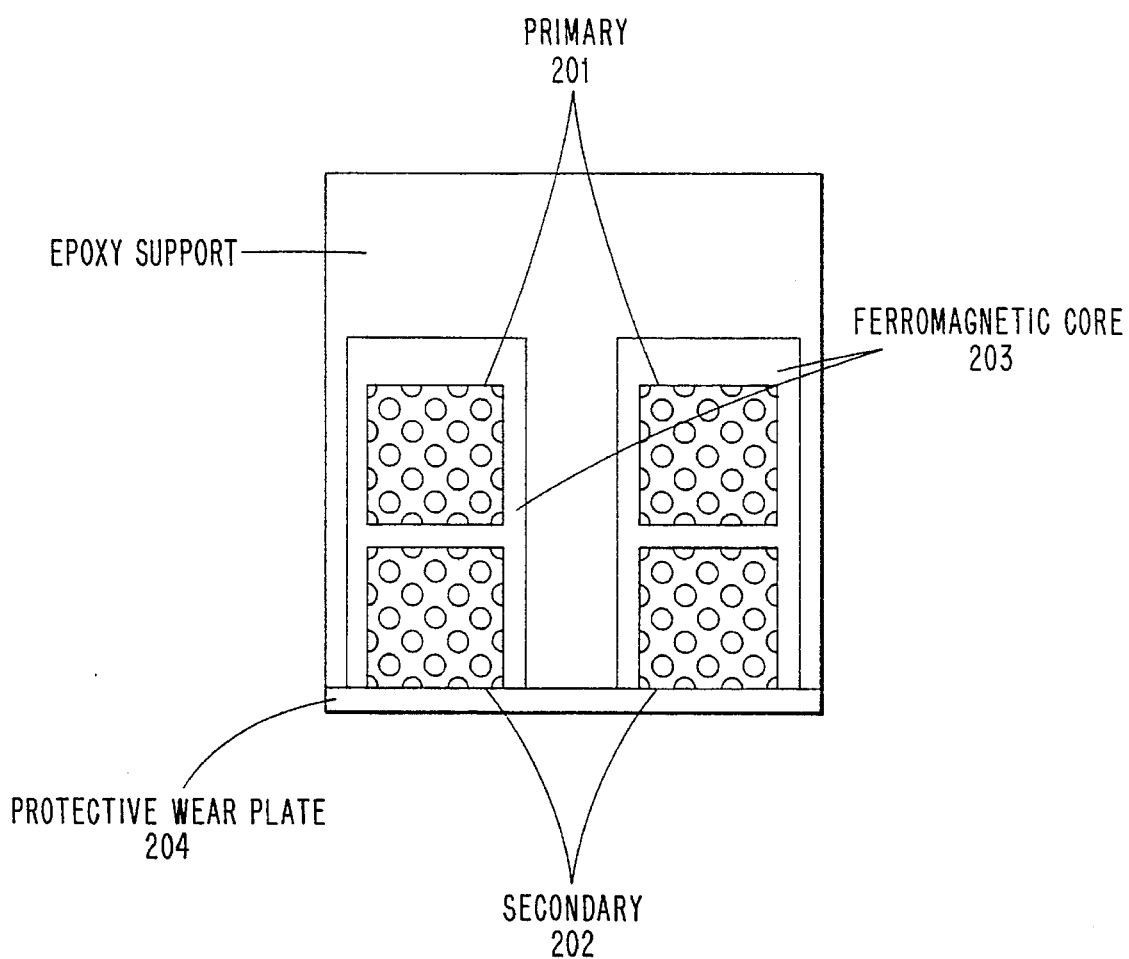
FIG. 2 illustrates a probe of the anodic capacity gauge of FIG. 1.

According to an exemplary embodiment of the present invention, FIG. 1 shows an oscillator 101 which can be used to provide a stable sinusoidal signal. This signal is amplified in amplifier 102 and applied to the primary coil 201 in the probe 107. The primary coil 201 is designed to generate an alternating magnetic field that is impressed on the zinc. A secondary coil 202 is provided to detect the magnetic fields generated by the eddy currents developed in the zinc and the primary coil 201. The two fields are then combined. The resulting voltage developed at the terminals of the secondary coil 202 represent the combined magnetic fields. Referring now to FIG. 2, to deliver a constant magnetic flux to the test article the primary coil 201 is driven with a constant peak to peak sinusoidal current. A ferromagnetic core material 203 is used to concentrate the magnetic field generated by the primary coil 201 and to focus the field received by the secondary coil 202. A non-conductive protective wear plate 204 provides a constant lift-off distance and protects the windings of the secondary coil.

Turning back now to FIG. 1, the secondary coil 202 is connected to a high impedance differential amplifier 103 to remove common mode noise and amplify the signal. By using a high impedance differential amplifier, the voltage induced in the secondary coil 202 will not be effected by wire resistance changes in the secondary. An RMS to DC converter 104 is used to convert the Root Mean Square amplitude of the secondary voltage to a DC voltage that is then converted to a digital representation using any one of a number of conventional analog to digital conversion techniques. A processor 106 is used to record the RMS amplitude of the secondary voltage. Using the techniques described below, the RMS amplitude information is related to equivalent Zn thickness units by the processor 106 and the Zn thickness units are displayed, or otherwise communicated, via interface 105. The operation of processor 106 to transform the amplitude signals into signals indicating Zn thickness, as well as exemplary embodiments of the present invention which provide for liftoff compensation and calibration will now be described.

The electrical properties of zinc make this metal an ideal candidate for eddy current inspection. At 20° C. Zinc has a resistivity of 5.9 $\mu\Omega$ cm and a conductivity of 1.70 siemens/m (i.e., 29% IACS (International Annealed Copper Standard)). When RMS voltage is plotted versus zinc thickness for a number of different excitation frequencies, it is seen that curves can be fit to relate RMS Voltage to zinc thickness. If these curves are constructed using zinc thickness samples prepared in a controlled manner with zinc of a known density, then the resulting zinc thickness derived from the curves can be used to determine the anodic capacity of the coating in equivalent zinc thickness units.

Figure 3:
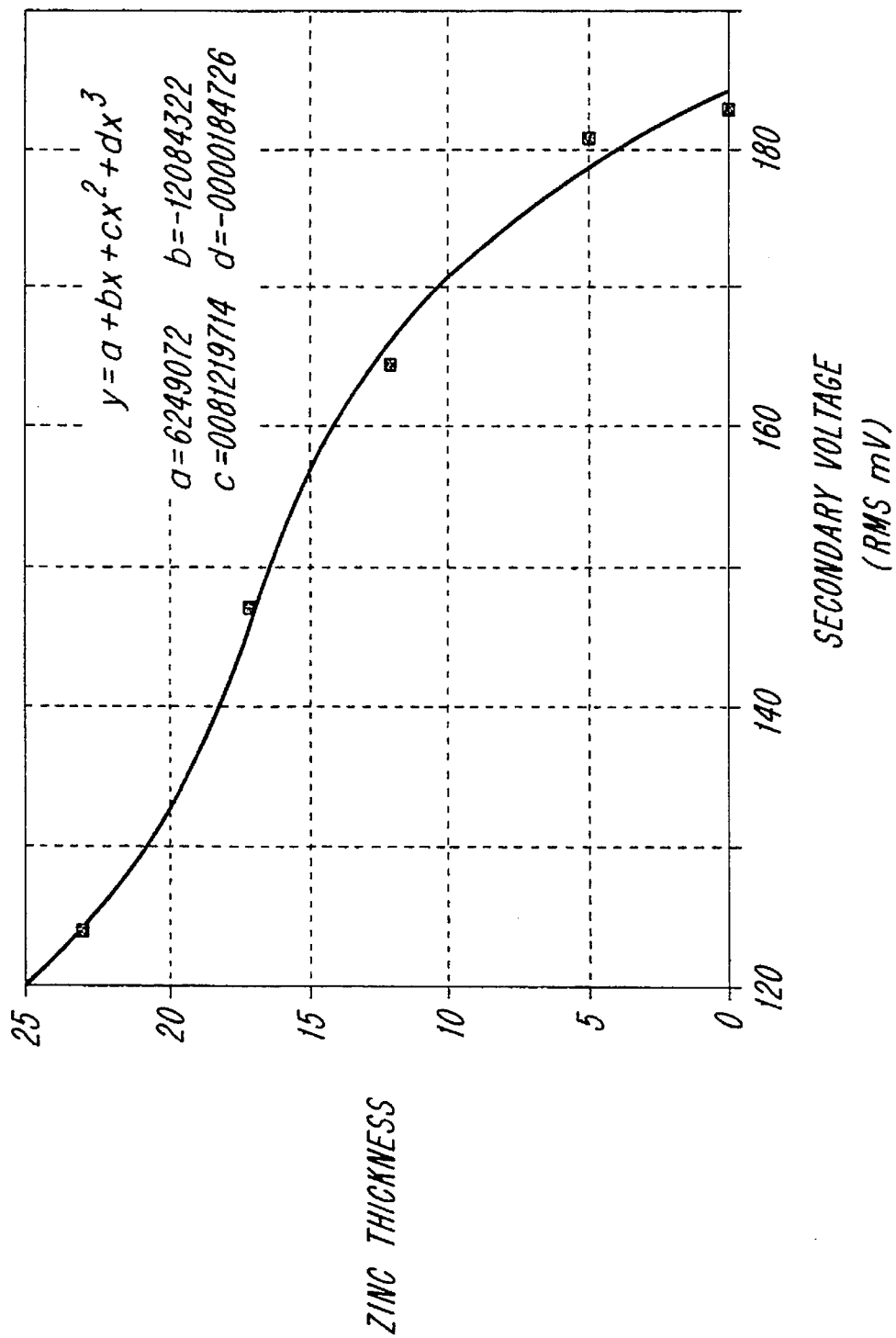
FIG. 3 illustrates a graph of zinc thickness versus secondary voltage.

An exemplary curve relating RMS secondary voltage to various zinc thickness samples having an 85% density is illustrated in FIG. 3. To create the curve from the samples taken, a polynomial curve fit can be performed on the data using known techniques to determine a polynomial approximation of the curve which can be represented as:

$$y=a+bx+cx^2+dx^{3+} \ldots$$

where:

x=RMS secondary voltage;

y=Coating thickness; and a,b,c,d . . . are constants to be determined such that the curve approximates the data samples.

Once a relationship is established between RMS voltage in the secondary and zinc thickness, the polynomial formula can be stored in processor 106 so that the RMS secondary voltages can be translated into equivalent Zn thickness units, e.g., Zn mils, to indicate the anodic capacity of the coating. Thus, if the exemplary curve of FIG. 3 was used in measuring anodic capacity, the Zn rail measurement would be standardized to zinc coatings having an 85% zinc density.

Alternatively, the formula can be solved for some predetermined number of likely RMS secondary voltages and the resulting Zn thickness values can be stored in a look-up table (not shown) in processor 106. If a relatively small look-up table is provided and greater resolution is desired, the processor 106 can interpolate between stored values when an RMS voltage is received that does not correspond to a particular stored value.

If all zinc coatings were identical and uncorroded then systems and methods similar to that described above, i.e., a single curve relating RMS voltage to zinc thickness without liftoff compensation, would suffice. Unfortunately zinc coatings differ both as applied, for example in zinc density, and later after the above-described corrosive effects transpire. Thus, the following exemplary embodiments illustrate how these coating changes can be taken into account to provide an operator with consistent and meaningful anodic protection measurements.

The electrical properties of thermally sprayed zinc do not change on an atomic scale, but the density of the applied zinc affects the resistivity of coated samples. Depending on the spray technique, the zinc density of the coating can be, for example, as low as 80% or as high as 95% of the bulk density (i.e., wire density). The resistivity of the coating is thus affected in a similar fashion. For example, testing has shown that flame sprayed zinc at a coating thickness of 4 mils has a density of 89% of the wire density and a resistivity of 7$\mu\Omega$ cm.

Changes in zinc coating density will also affect anodic capacity. A higher density of zinc in the coating will provide a greater degree of protection. Since the magnitude of the RMS secondary voltage decreases with decreasing resistivity (increased density), the processor 106 can display the coating thickness in equivalent anodic protection terms at interface 105. For example, if a 10 mil coating of 90% dense Zn is measured using an instrument calibrated using 85% dense Zn thickness standards, the instrument will report the thickness of the coating as being thicker than 10 mils. While such a measurement does not necessarily report an actual zinc thickness value, a measurement relative to a standard is valuable in that it characterizes anodic protection in terms of a single variable, thickness, with the other variable, density, being assumed. In the above example, the instrument has thus reported that the coating has an equivalent of $10^+$ mils of anodic protection as referred to the 85% dense Zn coating standard.

As the density of coatings vary, so do the relationships between the RMS voltages and Zn thickness values. This can be seen by the various exemplary curves illustrated in FIG. 4. Although exemplary curve A (501) may be suitable for most applications to provide measurements relative to a standard density, there may also be applications where the indication of an actual coating thickness is desirable. Thus, according to another exemplary embodiment of the present invention, an operator can adjust the instrument to measure a coating having an unknown density by using a sample of the coating having a known thickness to perform a single point recalibration as will now be described.

Figure 4:
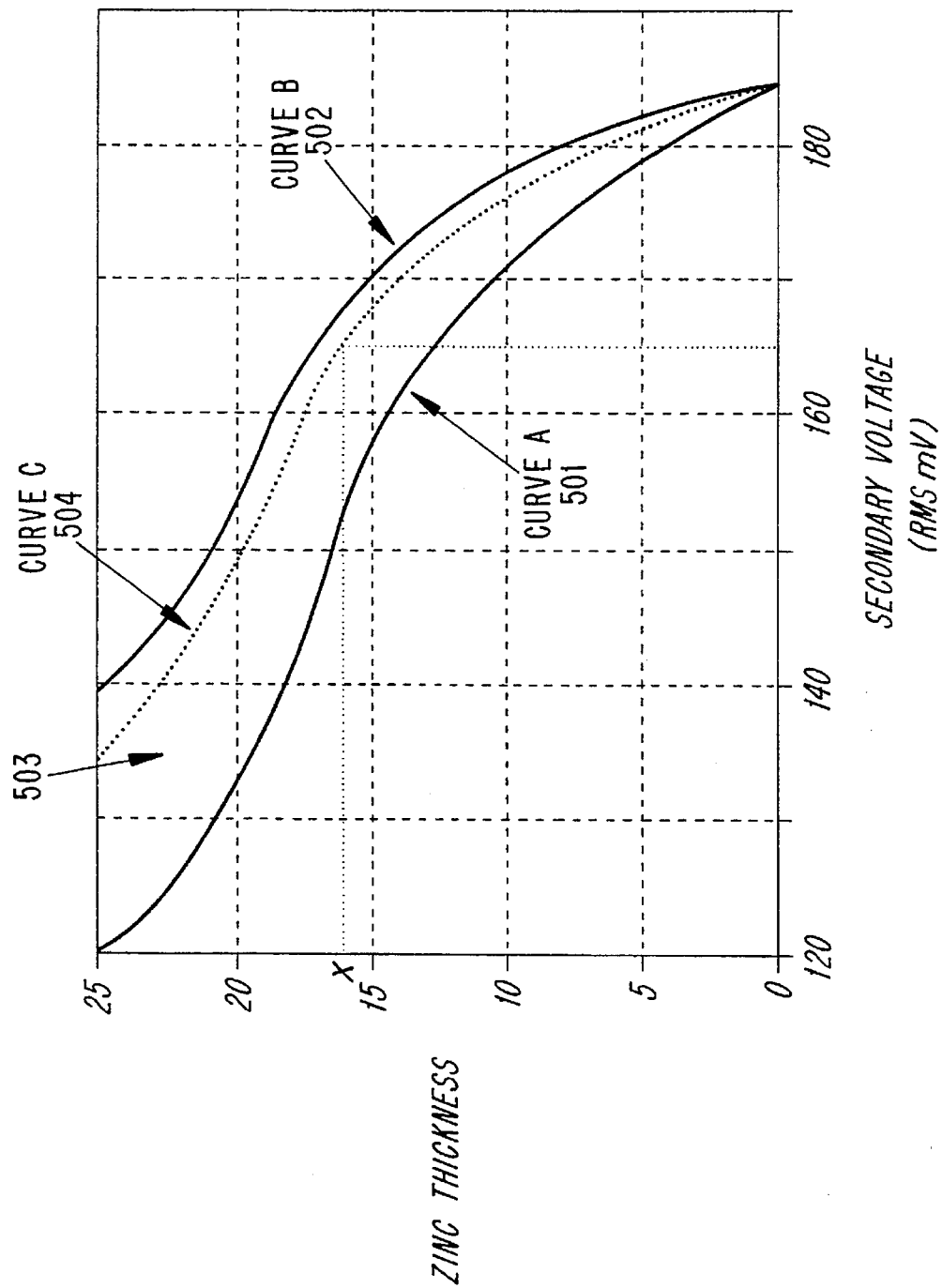
FIG. 4 illustrates exemplary stored curves and a recalibration curve.

As illustrated in FIG. 4, the locus of the curves A and B is at zero thickness. Two curves can be used by processor 106 to bound the recalibration. For example, curve B (502) can be constructed using a low density zinc coating standard, for example 79%, while curve A (501) can be constructed using a high density zinc coating standard, for example 85%. Although specific percentages are provided to illustrate this point, those skilled in the art will readily appreciate that the low density zinc coating standard can be varied within any range of statistically reasonable densities, e.g., 70–85%, and similarly the high density standard can also vary, for example between 80–95%.

Using the curves 501 and 502 as boundaries, a valid operation area is defined by region 503. Within region 503 user calibration adjustments are permitted. For example, curve A can be described as:

$$fA(x)=yA=aA+bAx+cAx^2+dAx^3 \ldots$$

and curve B can be described as:

$$fB(x)=yB=aB+bBx+cBx^2+dBx^3 \ldots$$

where x is the thickness of the sample used to recalibrate.

Then the single point recalibration adjustment factor can be calculated in processor 106 at thickness x by:

$$\alpha=(\text{operator reading}-fA(x))/(fB(x)-fA(x)).$$

Thus, when the exemplary apparatus of FIG. 1 has measured the sample, the processor 106 determines α and applies this adjustment factor to subsequent coating measurements as follows:

$$\text{thickness reading} = fA(x) + \alpha X \, (fB(x) - fA(x))$$

In this way, an actual zinc thickness reading will be provided at interface 105 either as an alternative to, or at the same time as, a reading which is relative to a known density standard. In practice the operator could thus measure a single point on the structure destructively using, for example, the masking tape method described above. The gauge could then be adjusted to read the desired thickness x. The instrument then determines α. Further readings are thus corrected as illustrated by curve C (504). According to an exemplary embodiment of the invention, α can be initially set to zero and an input capability provided at the interface 105 for the operator to reset α to zero for subsequent single point recalibrations.

Having dealt with zinc coatings of varying densities, corrosion effects will now be considered. According to exemplary embodiments of the present invention, lift-off compensation can reduce the effects of coating roughness and nonconductive corrosion and measure remaining anodic capacity through corrosion. For example if an operator were to measure a zinc coating that originally was 16 mils thick after one-half of its service life, a reading of approximately 8 Zn mils should be provided at interface 105 even though the actual thickness of the remaining zinc and zinc chloride as measured by a micrometer might be 16 mils or more.

The effects of lift-off on the magnitude of the RMS secondary voltage (Zp) decrease as the original zinc thickness of the sample decreases. For a detailed discussion of the effects of lift-off and other characteristics which impact eddy current inspection generally, the reader is referred to the "Manual on Eddy Current Method" published November, 1981 by Atomic Energy of Canada Limited and authored by Cecco et al, pp. 69–78, which disclosure is incorporated here by reference. As such, the operating frequency of oscillator 101 can be selected, for example, to provide maximum sensitivity in the secondary coil 202 for operation at a greatest expected coating thickness. Since thermally sprayed zinc is usually applied in thicknesses between 5–30 mils, the frequency can be chosen which will provide maximum sensitivity at 30 mils.

If the value of electrical resistivity ρ is chosen to be the lowest value that is possible in a zinc spray application then test frequency can be chosen so that sensitivity of the secondary coil is maintained even for the worst case spray characteristics. As mentioned earlier, field testing has shown that the maximum zinc density that is typically found in a coating is approximately 89% of the bulk density when flame spray techniques are used. The ρ for a coating of this density is approximately 7 μΩ cm.

An optimal frequency can be calculated based on the depth of penetration required. A good approximation is provided by $t/\delta = 0.8$, where t is the thickness and δ is the depth, i.e., referring to the penetration depth of the eddy currents. Thus, $f = 2560 \, \rho/t^2$ KHz, where f is the test frequency in KHz, ρ is the electrical resistivity in μΩ cm, and t is the thickness in rail. Accordingly, for the above described example, the test frequency can be calculated to be approximately 20 KHz for a maximum coating thickness of 30 mils. Although the exemplary apparatus of FIG. 1 is illustrated as including a fixed frequency oscillator 101, according to another exemplary embodiment of the present invention, the test frequency could be varied by processor 106 to optimize secondary coil sensitivity to coatings of known or approximated thicknesses.

According to another exemplary embodiment, information relating to the spray technique used to apply the zinc layer can be input to the gauge. Such information can include, for example, the ambient temperature at which the zinc layer was deposited, the spraying technique used (e.g. arc voltage) and any other factors which might affect the characteristics of the zinc layer. This information is then used by the processor 106 to select an appropriate calibration curve for use in subsequent measurements.

Although the present invention has been described in terms of the foregoing exemplary embodiments, those skilled in the art will appreciate that the present invention can be embodied in other forms. For example, although the exemplary apparatus of FIG. 1 is illustrated using an RMS-DC converter 104, both phase and amplitude information could be returned to processor 106 and used to determine coating thickness in a known manner. Moreover, as mentioned earlier, the present invention can readily be applied to other types of coatings such as titanium and zinc alloys.

Thus, the above-described exemplary embodiments are intended to be illustrative in all respects, rather than restrictive, of the present invention. Thus the present invention is capable of many variations in detailed implementation that can be derived from the description contained herein by a person skilled in the art. All such variations and modifications are considered to be within the scope and spirit of the present invention as defined by the following claims.

What is claimed is:

1. A gauge for measuring an anodic capacity of a coating comprising:

an oscillator for applying a test signal at a predetermined frequency;

an amplifier for amplifying said test signal;

a probe having a primary coil for applying said amplified test signal to said coating to produce eddy currents therein and a secondary coil which measures electrical effects of said eddy currents;

a converter for receiving an output signal from said secondary coil and converting said output signal into a digital pulse stream representative of the voltage induced into said secondary coil;

a processor for receiving said digital pulse stream, said processor including:
   a memory for storing data relationships between said voltage and coating thickness; and
   means for transforming said digital pulse stream using said stored data relationships into units of anodic capacity which are based upon both coating thickness and a standardized density; and an interface for outputting said anodic capacity.

2. The gauge of claim 1, wherein said coating comprises one of zinc, titanium, and a zinc/aluminum alloy.

3. The gauge of claim 1, wherein said stored data relations include a first curve relating voltage to coating thickness for a high density coating and a second curve relating voltage to coating thickness for a low density coating.

4. The gauge of claim 3, wherein said high density coating is within the range of 80–95% and said low density coating is within the range of 70–85% said high density being greater than said low density.

5. The gauge of claim 4, wherein said high density coating is 85%, said low density coating is 79% and said standardized density is one of said high and low densities such that said anodic capacity is provided relative thereto.

6. The gauge of claim 1, wherein said processor can also be used to generate an actual coating thickness value and said memory also stores a measured sample value, said processor further comprising:

means for determining a correction factor using said measured sample value and values of said first and second curves at a same thickness as a sample used to generate said measured sample value; and means for translating said voltage into an actual coating thickness value using one of said first and second curves and said correction factor, wherein said interface means is also for outputting said actual coating thickness.

7. A method for measuring anodic capacity in a coating comprising the steps of:

storing at least two calibration curves, each associated with different coating densities;

inspecting said coating using eddy current inspection techniques to return an induced voltage value;

transforming said induced voltage value into an anodic capacity measurement using one of said calibration curves; and outputting said anodic capacity measurement.

8. The method of claim 7 further comprising the steps of:

measuring a sample of said coating having a known thickness;

determining a correction factor to be applied to said one of said calibration curves based upon said induced voltage value and values of said at least two calibration curves at said known thickness to create a corrected calibration curve;

using said corrected calibration curve to determine an actual thickness value of said coating; and outputting both said anodic capacity measurement and said actual thickness value of said coating.

9. A gauge for measuring remaining anodic capacity of a zinc coating which has been thermally sprayed onto a reinforced concrete structure, the gauge comprising:

an oscillator for applying a test signal at a predetermined frequency;

an amplifier for amplifying said test signal;

a probe having a primary coil for applying said amplified test signal to said coating to produce eddy currents therein and a secondary coil which measures electrical effects of said eddy currents;

a converter for receiving an output signal from said second coil and converting said output signal into a digital pulse stream representative of the voltage induced into said secondary coil;

a processor for receiving said digital pulse stream, said processor including:

a memory for storing data relationships for a selected standard density of zinc in said zinc coating between said voltage and coating thickness; and means for transforming said digital pulse stream into anodic capacity units by comparing values represented by the digital pulse stream with the stored data relationships; and an interface for outputting said anodic capacity units.

10. A method for measuring remaining anodic capacity of a thermally sprayed zinc coating comprising the steps of:

storing at least two calibration curves, each associated with different zinc coating densities;

inspecting said thermally sprayed zinc coating using eddy current inspection techniques to return an induced voltage value;

transforming said induced voltage value into an anodic capacity measurement using one of said calibration curves, which anodic capacity measurement reflects the remaining anodic capacity of the thermally sprayed zinc coating relative to the zinc coating density of said one of said calibration curves; and outputting said anodic capacity measurement.

* * * * *